US011602588B2

(12) United States Patent
Assell et al.

(10) Patent No.: US 11,602,588 B2
(45) Date of Patent: Mar. 14, 2023

(54) CONNECTIVE TISSUE PROGENITOR CELL ASPIRATION AND PROCESSING SYSTEM

(71) Applicant: Fortus Medical, Inc., Minneapolis, MN (US)

(72) Inventors: Robert Assell, Minneapolis, MN (US); Andy Freeman, Minneapolis, MN (US)

(73) Assignee: ForCyte Medical, LLC, Marietta, GA (US)

( * ) Notice: Subject to any disclaimer, the term of this patent is extended or adjusted under 35 U.S.C. 154(b) by 0 days.

(21) Appl. No.: 15/996,765

(22) Filed: Jun. 4, 2018

(65) Prior Publication Data

US 2018/0353206 A1    Dec. 13, 2018

Related U.S. Application Data

(60) Provisional application No. 62/516,502, filed on Jun. 7, 2017.

(51) Int. Cl.
*A61B 17/16* (2006.01)
*A61M 1/00* (2006.01)
(Continued)

(52) U.S. Cl.
CPC ......... *A61M 1/892* (2021.05); *A61B 17/1635* (2013.01); *A61B 17/3472* (2013.01);
(Continued)

(58) Field of Classification Search
CPC .............. A61B 10/25; A61B 2217/005; A61B 17/1635; A61B 17/3472;
(Continued)

(56) References Cited

U.S. PATENT DOCUMENTS 4,969,870 A    11/1990 Kramer
5,152,763 A    10/1992 Johnson
(Continued)

FOREIGN PATENT DOCUMENTS

DE    19949866 A1    11/2001
WO    1999/59500 A2    11/1999

OTHER PUBLICATIONS

Mclain, et al. "Transpedicular aspiration of osteoprogenitor cells from the vertebral body: progenitor cell concentration affected by serial aspiration", The Spine Journal, Oct. 19, 2009, vol. 9, No. 12, pp. 995-1002.
(Continued)

*Primary Examiner* — Nathan R Price
*Assistant Examiner* — Tania Ismail
(74) *Attorney, Agent, or Firm* — Michael A. Bondi; Moss & Barnett

(57) ABSTRACT

A method of treating soft tissue conditions. A harvesting device is provided. The harvesting device is operably connected to a tissue processing device using tubing. An aperture is formed in a bone. The bone has an interior. The harvesting device is inserted through the aperture in the bone and into the interior of the bone. The harvesting device is manipulated to dissociate connective tissue progenitor cells in the interior of the bone. Tissue is aspirated from the interior of the bone. The connective tissue progenitor cells are separated from the aspirated tissue. The separated connective tissue progenitor cells are injected in a region of a body that is experiencing a soft tissue condition to treat the soft tissue condition.

18 Claims, 4 Drawing Sheets

(51) Int. Cl.
| | |
|---|---|
| A61B 17/34 | (2006.01) |
| A61K 9/00 | (2006.01) |
| A61K 35/28 | (2015.01) |
| A61M 1/02 | (2006.01) |
| C12M 1/00 | (2006.01) |
| A61B 10/02 | (2006.01) |
| A61B 17/32 | (2006.01) |
| A61L 27/38 | (2006.01) |

(52) U.S. Cl.
CPC ............ *A61K 9/0019* (2013.01); *A61K 35/28* (2013.01); *A61M 1/0281* (2013.01); *C12M 45/00* (2013.01); *A61B 10/025* (2013.01); *A61B 2010/0258* (2013.01); *A61B 2017/320064* (2013.01); *A61B 2217/005* (2013.01); *A61L 27/3856* (2013.01); *A61M 1/79* (2021.05); *A61M 2202/0429* (2013.01); *A61M 2202/09* (2013.01); *A61M 2205/3389* (2013.01); *A61M 2205/583* (2013.01); *A61M 2205/7545* (2013.01); *A61M 2210/02* (2013.01)

(58) Field of Classification Search
CPC .......... A61B 2017/320064; A61M 2202/0429; A61L 27/3856
See application file for complete search history.

(56) References Cited

U.S. PATENT DOCUMENTS

| | | |
|---|---|---|
| 5,269,785 A | 12/1993 | Bonutti |
| 5,456,267 A | 10/1995 | Stark |
| 5,624,418 A | 4/1997 | Shepard |
| 5,807,353 A | 9/1998 | Schmitz |
| 5,824,084 A | 10/1998 | Muschler |
| 6,022,354 A | 2/2000 | Mercuri |
| 6,049,026 A | 4/2000 | Muschler |
| 6,132,448 A | 10/2000 | Perez |
| 6,406,454 B1 | 6/2002 | Hajianpour |
| 6,673,629 B2 | 1/2004 | Yoshimura |
| 6,723,131 B2 | 4/2004 | Muschler |
| 6,981,948 B2 | 1/2006 | Pellegrino |
| 8,109,919 B2 | 2/2012 | Kraft |
| 8,137,408 B2 | 3/2012 | Kadiyala |
| 8,343,133 B2 | 1/2013 | Allee |
| 8,439,929 B1 | 5/2013 | Sharratt |
| 8,579,912 B2 | 11/2013 | Isaza |
| 8,852,119 B2 | 10/2014 | Wawrzyniak |
| 2002/0058945 A1 | 5/2002 | Steiner |
| 2002/0082519 A1 | 6/2002 | Miller |
| 2002/0161449 A1 | 10/2002 | Muschler |
| 2003/0031695 A1 | 2/2003 | Kadiyala |
| 2004/0071668 A1 | 4/2004 | Barry |
| 2005/0101963 A1 | 5/2005 | Merboth |
| 2005/0130301 A1 | 6/2005 | McKay |
| 2006/0246150 A1 | 11/2006 | Thorne |
| 2006/0264964 A1 | 11/2006 | Scifert |
| 2006/0273049 A1 | 12/2006 | Leach |
| 2007/0055282 A1 | 3/2007 | Muschler |
| 2007/0198043 A1 | 8/2007 | Cox |
| 2008/0103605 A1 | 5/2008 | Kadiyala |
| 2008/0145392 A1 | 6/2008 | Knaack |
| 2008/0195115 A1 | 8/2008 | Oren |
| 2008/0283474 A1 | 11/2008 | Leach |
| 2008/0288006 A1 | 11/2008 | Brannon |
| 2009/0014391 A1 | 1/2009 | Leach |
| 2009/0081689 A1 | 3/2009 | Yamanishi |
| 2009/0137927 A1 | 5/2009 | Miller |
| 2009/0187116 A1 | 7/2009 | Noishiki |
| 2009/0287190 A1 | 11/2009 | Shippert |
| 2011/0257557 A1 | 10/2011 | Pesce |
| 2012/0116247 A1 | 5/2012 | Wawrzyniak |
| 2013/0030547 A1 | 1/2013 | Burkinshaw |
| 2013/0131545 A1 | 5/2013 | Azimpoor |
| 2014/0100574 A1 | 4/2014 | Bono |
| 2014/0105960 A1 | 4/2014 | Zoldan |
| 2014/0257133 A1 | 9/2014 | Landrigan |
| 2014/0274894 A1 | 9/2014 | Leach |
| 2014/0323914 A1 | 10/2014 | VanderWoude |
| 2014/0363403 A1* | 12/2014 | Segina .................. A61K 35/28 424/93.7 |
| 2015/0110890 A1 | 4/2015 | Assell |
| 2015/0164949 A1 | 6/2015 | Sowemimo-Coker |
| 2015/0182268 A1 | 7/2015 | Donner |
| 2015/0273360 A1 | 10/2015 | King |
| 2016/0325018 A1 | 11/2016 | Assell |
| 2016/0331878 A1 | 11/2016 | McGillicuddy |
| 2018/0353206 A1 | 12/2018 | Assell |

OTHER PUBLICATIONS

Duguy N., et al.: "Biomaterials and osseous regeneration", Annales De Chirurgie Plastique Esthetique, Expansion Scientifique Francaise, Paris, France, vol. 45, No. 3, Jun. 1, 2000, pp. 364-376, Issn: 0294-1260.

Ripamonti U., et al., "Tissue Engineering of Bone by Osteoinductive Biomaterials", MRS Bulletin, Pittsburgh, US, vol. 21, No. 11, Nov. 1, 1996, XP008005014, pp. 36-39.

Kurita, et al., "Differential Effects of Three Preparations of Human Serum on Expansion of Various Types of Human Cells", American Society of Plastic Surgeons, Dec. 20, 2007, 12 pgs.

International Search Report and Written Opinion received for PCT/US2018/035810, dated Aug. 23, 2018, 11 pgs.

International Preliminary Report on Patentability received in PCT/US2018/035810 dated Dec. 19, 2019, 9 pgs.

International Search Report and Written Opinion received for PCT Serial No. PCT/US2021/018570 dated May 7, 2021, 9 pgs.

\* cited by examiner

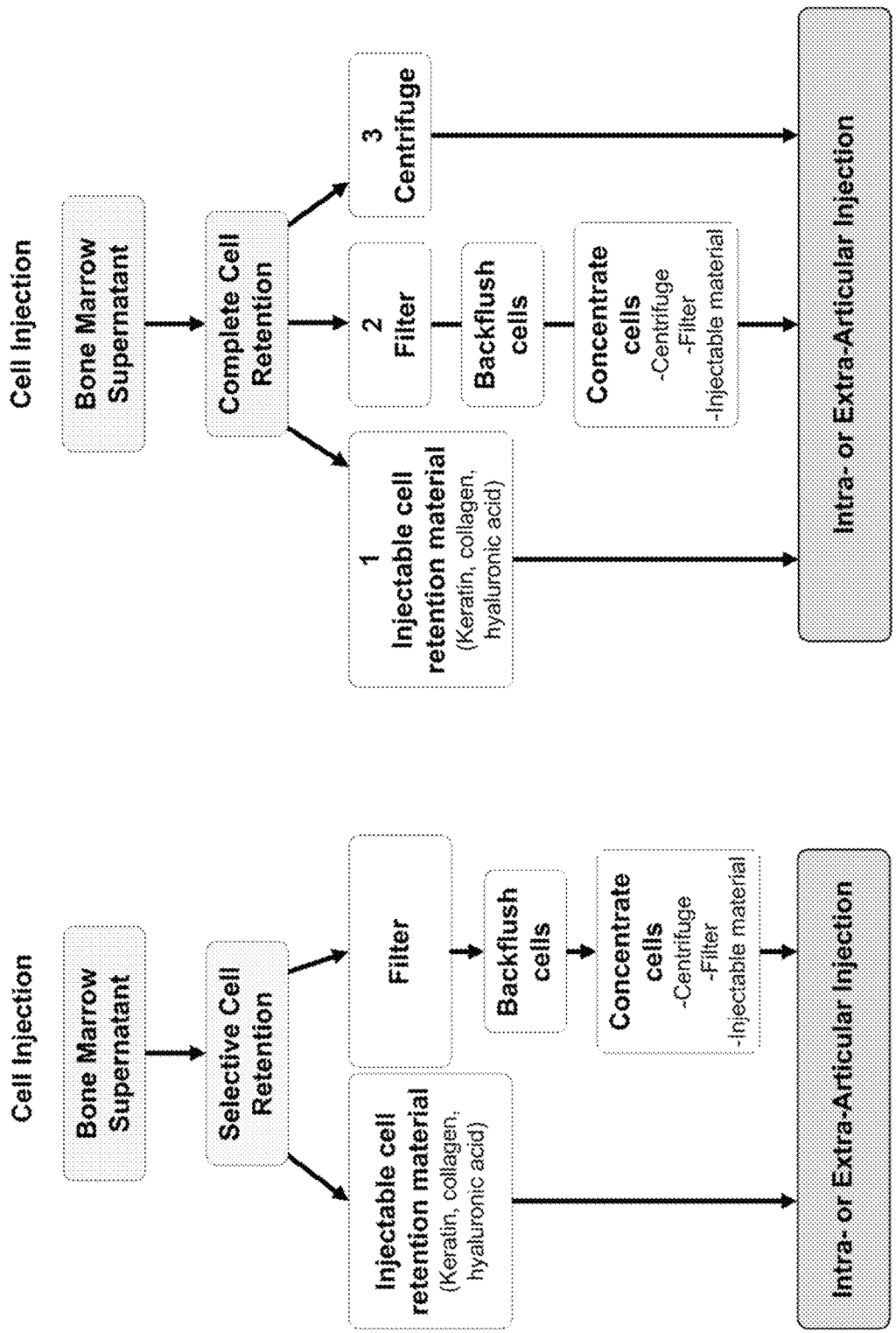

CONNECTIVE TISSUE PROGENITOR CELL ASPIRATION AND PROCESSING SYSTEM

REFERENCE TO RELATED APPLICATION

This application claims priority to Provisional Applic. No. 62/516,502, filed on Jun. 7, 2017, the contents of which are incorporated herein by reference.

FIELD OF THE INVENTION

The invention relates generally to products for treatment of soft tissue conditions. More particularly, the invention relates to a connective tissue progenitor cell aspiration and processing system.

BACKGROUND OF THE INVENTION

It has been recognized that connective tissue progenitor cells have beneficial uses in a variety of applications. For example, U.S. application Ser. Nos. 14/517,202; 15/150,089 and 15/150,121, which are all assigned to the assignee of the present application, and directed to different aspects of aspirating and processing bone marrow to prepare bone grafts.

Traditionally, doctors have used a large bore needle to aspirate marrow. However, orthopedic companies have developed their own versions of bone marrow aspirate concentrate systems for use specifically with bone graft substitute. These disposable kits are used for aspirating and concentrating the stem cells found in the bone marrow onto a graft matrix to be implanted into the patient. Combined with a bone graft substitute, bone marrow aspirate concentrate may provide similar results to an autograft (Geistlich, 2011).

An example of one such prior art bone marrow aspiration needle is disclosed in Allee et al., U.S. Pat. No. 8,343,133. This device includes a handle and a needle that extends therefrom. The needle has a central bore that in addition to facilitating the aspiration of the bone marrow also enables a guide wire to extend therethrough to facilitate accurate placement of the device in bone. The handle includes a port to which a syringe is attached to cause the bone marrow to be aspirated through the needle.

Landrigan et al., U.S. Patent Publication No. 2014/0257133, discloses a bone marrow aspiration needle that is fabricated from a flexible material. Landrigan indicates that the cannulated introducer needle can be curved to approximate the natural curvature of the iliac crest.

Wawrzyniak et al., U.S. Pat. No. 8,852,119, describes a flexible bone marrow aspiration needle having a helical groove in an outer surface thereof. An elastomeric overcoat covers at least a portion of the groove.

SUMMARY OF THE INVENTION

An embodiment of the invention is directed to a method of treating soft tissue conditions. A harvesting device is provided. The harvesting device is operably connected to a tissue processing device using tubing. An aperture is formed in a bone. The bone has an interior. The harvesting device is inserted through the aperture in the bone and into the interior of the bone. The harvesting device is manipulated to dissociate connective tissue progenitor cells in the interior of the bone. Tissue is aspirated from the interior of the bone. The connective tissue progenitor cells are separated from the aspirated tissue. The separated connective tissue progenitor cells are injected in a region of a body that is experiencing a soft tissue condition to treat the soft tissue condition.

Another embodiment of the invention is directed to a method of treating soft tissue conditions. A harvesting device is provided. The harvesting device is operably connected to a tissue processing device using tubing. An aperture is formed in a bone. The bone has an interior. The harvesting device is inserted through the aperture in the bone and into the interior of the bone. The harvesting device is manipulated to morcelize the interior of the bone and dissociate connective tissue progenitor cells in the interior of the bone. Tissue is aspirated from the interior of the bone. Bone fragments are separated from the aspirated tissue. Red blood cells are separated from the aspirated tissue using a binding agent that is capable of selectively binding with the red blood cells in the aspirated tissue. The connective tissue progenitor cells are separated from the aspirated tissue using a filter material that is associated with the tissue processing device. The separated connective tissue progenitor cells are hydrated. The separated connective tissue progenitor cells are injected in a region of a body that is experiencing a soft tissue condition to treat the soft tissue condition.

Another embodiment of the invention is directed to a therapeutic composition for treating soft tissue conditions. The therapeutic composition includes connective tissue progenitor cells and an injectable cell retention material. The connective tissue progenitor cells are substantially devoid of red blood cells.

Another embodiment of the invention is directed to a method of treating a soft tissue condition. A therapeutic composition is prepared that includes connective tissue progenitor cells and an injectable cell retention material. The connective tissue progenitor cells are substantially devoid of red blood cells. The therapeutic composition is injected into a living body experiencing the soft tissue condition.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 6 is a flow chart illustrating processes for forming the bone marrow into an injectable material for use in treating soft tissue conditions that utilizes selective cell retention.

FIG. 7 is a flow chart illustrating processes for forming the bone marrow into an injectable material for use in treating soft tissue conditions that utilizes complete cell retention.

DETAILED DESCRIPTION OF THE INVENTION

Figure 1:
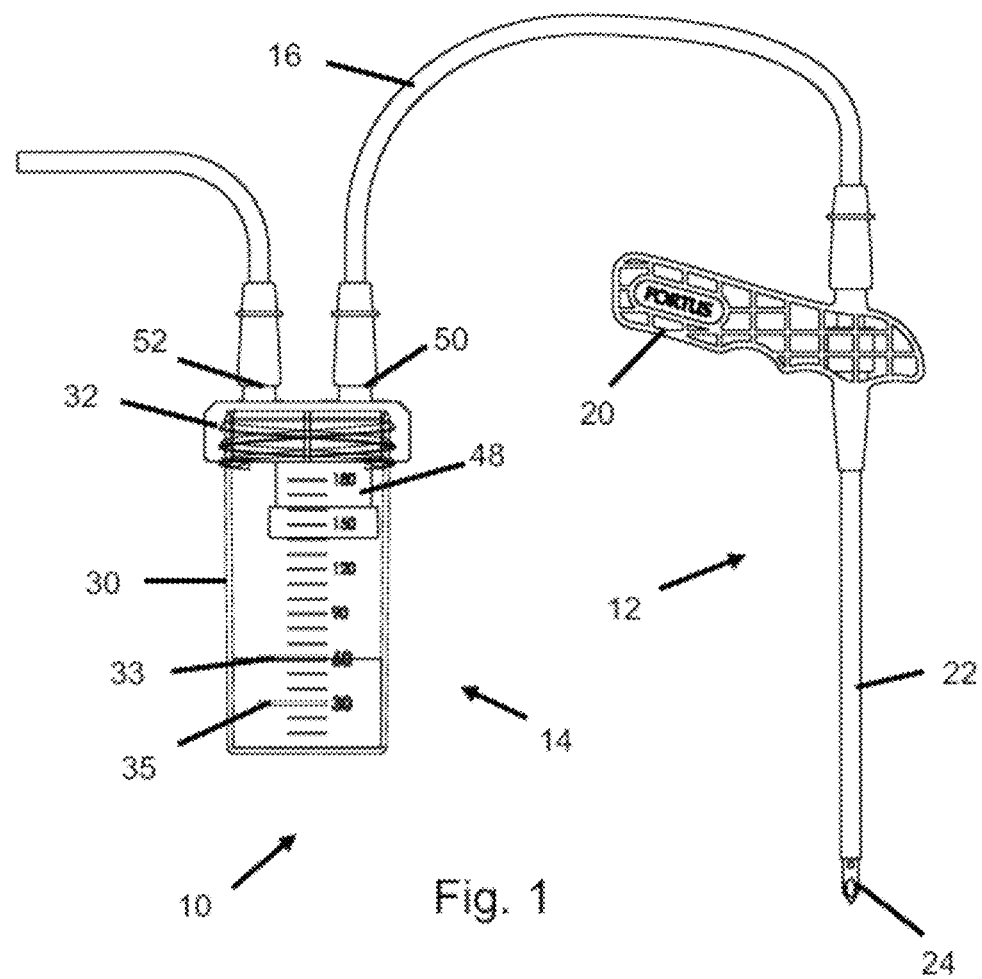
FIG. 1 is a side view of a connective tissue progenitor cell harvesting and processing system according to an embodiment of the invention.

An embodiment of the invention is directed to a connective tissue progenitor cell harvesting and processing system, which is illustrated in FIG. 1. The connective tissue progenitor cell harvesting and processing system 10 generally includes a harvesting device 12 that is operably attached to a tissue processing device 14 with tubing 16.

As used herein, connective tissue progenitor cells are intended to encompass multi-potent cells that can differentiate to become osteoblasts, chondrocytes, myocytes, and adipocytes. These cells are sometimes referred to as mesenchymal stem cells.

The connective tissue progenitor cell harvesting and processing system 10 facilitates extraction of connective tissue progenitor cells from a patient and such extracted cells are then used in preparing a connective tissue progenitor cell containing product, as is described in more detail herein. In certain embodiments, this product is particularly suited for treating a variety of soft tissue conditions, examples of which include osteoarthritis and inflamed/damaged ligaments.

A significant advantage of the invention is that it is a contained system, which facilitates use of the invention in an operating room as well as in an out-patient setting. The invention thereby enables treatment products to be prepared using materials aspirated from the patient in a cost-effect manner proximate to when it is desired to use the treatment products. The invention thereby provides a completely autologous process that enables use of the patient's own tissue in preparing treatment products.

The harvesting device 12 includes a handle portion 20 and a needle portion 22 that are operably connected to each other. In certain embodiments, the needle portion 22 is detachably connected to the handle portion 20. In other embodiments, the needle portion 22 is integrally formed with the handle portion 20.

In certain embodiments, the needle portion 22 may have an outer diameter of about 6 millimeters. A central bore 23 extends through the needle portion 22. While it is desired to minimize the formation and aspiration of bone chips during the process, forming the needle portion 22 with this diameter minimizes the potential that bone fragments will become stuck while being drawn through the needle portion 22 during the aspiration process.

The needle portion 22 having the preceding characteristics may have a two-part configuration that includes a shaft portion and a tip portion 24. The shaft portion may include an inner shaft and an outer shaft. The inner shaft may be fabricated from a metallic material such as stainless steel. The metallic material thereby provides the needle portion 22 with a relatively high strength while having a relatively thin wall thickness.

In certain embodiments, the wall thickness of the metallic material may be less than about 10 thousandths of an inch. In certain embodiments, the wall thickness of the inner shaft is between about 3 and 6 thousandths of an inch. In still other embodiments, the wall thickness of the inner shaft is about 4 thousandths of an inch.

Fabricating the inner shaft with a relatively thin wall thickness allows the inner channel to be relatively wide to facilitate a large flow rate of tissue (and potentially bone fragments) therethrough while at the same time having a relatively small outer diameter to minimize the size of the hole that is formed in the bone to access the interior of the bone where the connective tissue progenitor cells are located.

The outer shaft may be fabricated from a polymeric material that is molded over the inner shaft. The outer shaft thereby enhances strength of the inner shaft while allowing the needle portion 22 to deflect during the tissue harvesting process. Deflecting of the needle portion 22 during the aspiration process minimizes the potential that the tip portion 24 will cause bone fragments to be formed by contact of the rigid parts inside of the bone by the tip portion 24.

The combined structure of the inner shaft and the outer shaft provides the needle portion 22 with enhanced torsional strength compared to a needle fabricated only from a metallic material or a polymeric material.

Another advantage of using the polymeric outer shaft over the metallic inner shaft is that it is possible for the bore that extends through the inner shaft to have a relatively constant size over the length of the shaft portion. If the shaft portion had been fabricated only from a polymeric material, it would have been necessary for the inner diameter to taper when moving from the proximal end to the distal end of the shaft portion to facilitate molding of the shaft portion.

Because of the length of the shaft portion, such tapering would have resulted in a relatively thick wall proximate the proximal end, a relatively thin wall proximate the distal end or combination thereof. Such differences in wall thickness would have limited the flexing of the shaft portion near the proximal end while providing too much flexibility proximate the distal end. Both of these situations would have limited the ability to maneuver the needle portion 22 during the tissue recovery process.

An outer diameter of the needle portion 22 may be wider proximate the handle portion 20. Using such a configuration increases the strength of the harvesting device 12 such that there is less likelihood of the harvesting device 12 deforming during the process of dissociating the connective tissue progenitor cells inside of the bone or when aspirating tissue from the bone.

Nerves are primarily located on the surface of the bone. The process of cutting or drilling through the surface of the bone disrupts the nerves and thereby leads to the patient experiencing pain. Because of the diameter of the coring device, the patient typically experiences significant pain in the autograft harvesting region and such pain limits the use of this procedure.

The harvesting device 12 described herein has an outer diameter of about 6 millimeters, which is significantly smaller than the coring device and this smaller size hole that extends through the bone surface represents a reduction of the hole of between about 60 and 90 percent when compared to the coring device.

The smaller hole associated with the harvesting device 12 described herein thereby results in significantly lower pain than the coring device described above and such significantly lower pain makes the tissue harvesting procedure described herein to be much more tolerable to patients.

To provide the needle portion 22 with a desired level of sharpness, the needle portion 22 has the tip portion 24 that is fabricated from a metallic material as the metallic material provides an enhanced sharpness as compared to a tip fabricated from a polymeric material. The tip portion 24 may be attached to the distal end of the inner tube before the outer tube is molded over the inner tube.

Figure 2:
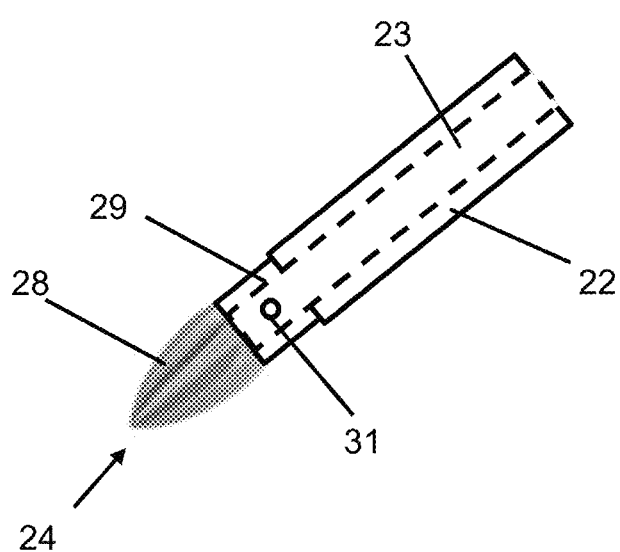
FIG. 2 is a perspective view of a needle for use in conjunction with the connective tissue progenitor cell harvesting and processing system of FIG. 1.

The tip portion 24, which is most clearly illustrated in FIG. 2, facilitates accessing the interior of a bone. The harvesting device 12 also facilitates disrupting tissue inside of the bone and thereby enhances the amount of the connective tissue progenitor cells that can be recovered from a patient. This process also increases the concentration of the connective tissue progenitor cells per unit volume that are recovered from the patient.

While it is desired for the tissue to be disrupted, it is also desirable to substantially minimize the formation of bone fragments during this process because the formation of bone fragments increases the likelihood that the bone fragments will be aspirated and such bone fragments are undesirable when preparing a product that is used in conjunction with treating soft tissue conditions. Minimizing the formation of the bone fragments reduces the need to separate the bone fragments from the connective tissue progenitor cells during the process of forming the treatment products.

One such tip configuration that minimizes the formation of bone fragments utilizes as fluted design such as illustrated in FIG. 2. At least a portion of the flutes has a sharpened surface or ridge 28. The shape of the tip portion 24 also causes any bone fragments thereby produced to be pushed aside as the needle portion 22 is inserted into the bone and such a process decreases the potential of the bone fragments being aspirated.

The sharpened surface 28 facilitates cutting while the needle portion 22 is inserted into and removed from the bone. The sharpened surface 28 also facilitates cutting tissue while the needle portion 22 is axially rotated and/or pivoted. In certain embodiments, the needle portion 22 is axially rotated as the tip portion 24 passes through the interior of the bone as such axial rotation causes tissue that comes into contact with the sharpened surface to be cut or macerated. This process dissociates connective tissue progenitor cells inside the bone and such process facilitates aspirating a higher concentration of the connective tissue progenitor cells.

Intermediate the tip portion 24 and the needle portion 22, a reduced diameter region 29 may be provided. The reduced diameter region 29 may have an outer diameter that is less than an outer diameter of the needle portion 22 that is adjacent thereto. The reduced diameter region 29 may also have an outer diameter that is less than an outer diameter of the tip portion 24. Using this structure facilitates forming a seal between the outer surface of the needle portion 22 and the tissue adjacent thereto. This configuration also facilitates flow of tissue from the tip portion 24 to the reduced diameter region 29 such that the tissue may be extracted through an aperture 31 in the reduced diameter region 29 that is in communication with the central bore 23 that extends along a length of the needle portion 22.

To minimize the aspiration of bone fragments, the aperture 31 may be formed with a relatively small size to prevent bone fragments having a size greater than the apertures 31 from passing through the apertures 31. There may be multiple apertures 31 provided on the device to enhance the rate at which the tissue can be withdrawn from the patient. Multiple apertures 31 may also minimize the potential of the aspiration process being interrupted by plugging of a significant portion of the apertures 31.

The tissue processing device 14 generally includes a collection vessel 30 to which a collection vessel cap 32 is operably attached as illustrated in FIG. 1. The collection vessel 30 may be formed with a size based upon the volume of tissue that is anticipated to be aspirated from the patient. In certain embodiments, the collection vessel 30 has a volume of about 180 cubic centimeters.

The collection vessel 30 may have a variety of shapes using the concepts of the invention. In certain embodiments, the collection vessel 30 has a generally cylindrical shape. Using such a shape enables the collection vessel cap 32 to be attached using a rotational motion.

A side of the collection vessel 30 may include at least two volume collected markers 33, 35. In one embodiment, the volume collected markers include an upper marker 33 and a lower marker 35. The upper marker 33 and the lower marker 35 thereby provide guidance to the person using the invention regarding whether a desired volume of tissue has been collected. In other embodiments, the volume collected markers may include a series of identifiers that correspond to a conventional volume measuring system such as milliliters.

Proximate an upper end of the collection vessel 30, an opening may be provided. In one such embodiment, the opening is generally circular and has a thread on a surface thereof that can be used when attaching the collection vessel cap 32 to the collection vessel 30. In certain embodiments, the thread may be on an outer surface of the opening. A person of skill in the art will appreciate that a variety of other techniques may be used to attach the collection vessel cap 32 to the collection vessel 30.

One aspect of the attachment of the collection vessel cap 32 to the collection vessel 30 is that a substantially air-tight seal is formed when the collection vessel cap 32 is attached to the collection vessel 30 so that a vacuum may be used to draw the aspirated tissue into the collection vessel 30.

The collection vessel 30 may be fabricated from a variety of materials using the concepts of the invention. In one embodiment, at least a portion of the collection vessel 30 is fabricated from a transparent material. Such a configuration enables a person using the connective tissue progenitor cell tissue harvesting and processing system 10 to not only view the volume of aspirated tissue in the collection vessel 30 but also other characteristics of the aspirated tissue such as a color of the aspirated tissue and/or the presence of discrete regions in the aspirated tissue.

Another criterion for the material that is used in fabricating the collection vessel 30 is that the material be biologically compatible and facilitate sterilization of the collection vessel 30 prior to use. An example of one such material that may be used to fabricate the collection vessel 30 is polycarbonate.

The collection vessel cap 32 may have a generally cylindrical configuration with an inner diameter that is selected based upon an outer diameter of the collection vessel 30 proximate the threaded region to facilitate removable attachment of the collection vessel cap 32 to the collection vessel 30. In this regard, the collection vessel cap 32 may include a thread on an inner surface thereof that is shaped generally complementary to the thread on the collection vessel 30.

While not illustrated, at least a portion of the outer surface of the collection vessel cap 32 may have a shape and/or texture that enhances the ability to grasp the collection vessel cap 32 and turn the collection vessel cap 32 with respect to the collection vessel 30. Because of the nature of the invention and the potential desire to remove the collection vessel cap 32, the collection vessel cap 32 is typically intended to be tightened and loosened using manual force.

The collection vessel cap 32 includes a first port 50 and a second port 52 formed therein. A person of skill in the art will appreciate that at least one of the first port 50 and the second port 52 may alternatively be formed in the collection vessel 30.

The first port 50 includes a connector that facilitates attachment to the tubing 16. In certain embodiments, the first port 50 enables tubing 16 to be attached and detached. When the tubing 16 is attached, a substantially gas-impervious seal is formed. The first port 50 may include a standardized connector profile that enables a variety of objects to be attached thereto. An example of one suitable standardized connector is marketed under the identifier Leur Lock.

Similar to the first port 50, the second port 52 may be formed with a standardized connector profile. An example of one such connector profile that can be used for the second port 52 is a tapered push-on connector that facilitates a friction connection. In certain embodiments, the push-on connector includes a plurality of ridges, which reduce the potential of the tubing or other object becoming detached from the second port 52.

The collection vessel cap 32 may be fabricated from a variety of materials using the concepts of the invention. In one embodiment, at least a portion of the collection vessel cap 32 is fabricated from a transparent material.

Another criterion for the material that is used in fabricating the collection vessel cap 32 is that the material be biologically compatible and facilitate sterilization of the collection vessel cap 32 prior to use. An example of one such material that may be used to fabricate the collection vessel cap 32 is acrylonitrile butadiene styrene.

A filter container 48 may be provided with respect to the tissue processing device 14 for separating bone fragments from the other aspirated tissue. The filter container 48 is positioned so that before the bone fragments and tissue flow into the collection vessel 30, these components pass through the filter container 48. The filter container 48 thereby facilitates separation of the bone fragments from the other portions of the aspirated tissue.

In certain embodiments, the filter container 48 is attached to an inner surface of the collection vessel cap 32. The filter container 48 may be removably attached to the collection vessel cap 32 such as using a threaded mechanism.

In other embodiments, the filter container 48 may be attached to an outer surface of the collection vessel cap 32. In such an embodiment, the first port 50 may be directly attached to the filter container 48. In still other embodiments, the filter container 48 may be separate from the tissue processing device 14. In this configuration, the tubing 16 is attached to the filter container 48. Another section of tubing (not shown) attached the filter container outlet to the first port 50.

The filter container 48 may have a volume that is significantly smaller than the volume of the tissue processing device 14. In certain embodiments, the filter container 48 has a volume of less than about 20 cubic centimeters. In other embodiments, the filter container 48 has a volume of about 15 cubic centimeters.

A surface of the filter container 48 may have perforations formed therein. In certain embodiments, a lower surface of the filter container 48 may be perforated having a plurality of openings formed therein. The size of the openings may be selected to retain substantially all of the bone fragments in the filter container 48 as the bone fragments and tissue are aspirated from the patient. On the other hand, the openings are sufficiently large so that the aspirated liquid is permitted to flow through the lower surface and into the collection vessel 30. The perforations thereby affect physical separation of the aspirate.

In certain embodiments, the lower surface is integrally formed with the other components of the filter container 48. In other embodiments, the lower surface may be removably attached to the filter container 48 such as using a threaded mechanism. This threaded mechanism may be similar to the threaded mechanism that is used to attach the filter container 48 to the collection vessel cap 32.

A filter material may at least partially fill the filter container 48. The filter material is selected with a pore size such that substantially all of the bone fragments are retained in the filter material.

The filter material may thereby provide physical separation of the bone fragments from the remainder of the material in the aspirate. Such a separation mechanism is referred to as physical separation.

The filter material may also have an affinity for the beneficial components in the aspirate such that as the beneficial components flow past the filter material, the beneficial components are attached to the filter material. The beneficial components are thereby retained in the filter container 48 would be included in the bone graft fabricated therefrom. For example, the filter material may have an affinity for the connective tissue progenitor cells.

In certain embodiments, the filter material is a biomaterial. In other embodiments, the filter material is a naturally occurring biocompatible material. One such biomaterial is solid when dry but that solubilizes when wet. Examples of suitable materials are collagen materials such as are marketed under the designations Helitene and Avitene, which are conventionally used to stop bleeding in wounds. Additional materials could be configured from keratin, collagen, hyaluronic acid, chondroitin, glucosamine, amniotic fluid, tissue from an amniotic sac, or any other biocompatible material that may or may not be hydrogels.

The supernatant is passed through the graft material quickly to retain all or selectively retain specific cells like connective tissue progenitor cells, without absorbing the supernatant fluid. The second step would be hydration of the material such as using saline, phosphate-buffered saline and water to form a cell suspension.

Certain substances have an affinity for connective tissue progenitor cells, which causes the selective cell retention. It is believed that this affinity may be associated with a surface charge of the connective tissue progenitor cells, which relates to zeta potential.

As used herein, passing the supernatant quickly through the graft material means the process takes less than about five minutes. In certain embodiments, the supernatant passes through the graft material in between about 60 and 90 seconds.

In another embodiment, the connective tissue progenitor cells are bound to a biopolymer, an example of which is keratin, to form a therapeutic composition. The product thereby produced not only benefits from the advantageous properties of the connective tissue progenitor cells but also benefits from the advantageous properties of the keratin.

It is also possible to use the connective tissue progenitor cells in conjunction with cells that are obtained from amniotic fluid and/or other portions of the amniotic sac. These components may be used alone or in conjunction with at least one biopolymer, an example of which is keratin.

In certain embodiments, the product thereby produced is in the form of hydrogel fibers or hydrogel beads. This product is suitable for use in a variety of applications, examples of which include bone graft and the compounds that are efficacious in treating soft tissue conditions, which are discussed in more detail in other portions of this patent application.

After the connective tissue progenitor cells bind to the hydrogel, the bound product hydrolyzes and becomes a gel. Such a gel facilitates delivery of the connective tissue progenitor cells to a location where the connective tissue progenitor cells may produce a beneficial result. The gel also enhances retention of the efficacious components in the area where such components may provide beneficial results in conjunction with the treatment of the soft tissue condition. In certain embodiments, a substantial portion of the connective tissue progenitor cells are retained proximate a location of the soft tissue condition.

A material like keratin hydrogel would be safe for injection in or near a joint. Another advantage of this configuration is that a small amount of filter material such as in the range of between about 1-2 cubic centimeters could be used to capture the cells with very high efficiency. As used herein, very high efficiency means that greater than about 70 percent by weight of the aspirated connective tissue progenitor cells are captures and, in certain embodiments, greater than about 90 percent by weight of the aspirated connective tissue progenitor cells are captured.

In still another embodiment, it is possible to use biomaterial hybrid materials such as combinations of keratin and at least one of tricalcium phosphate, poly-lactic acid, poly-glycolic acid, poly-caprolactone and hyaluronic acid. These materials may be used in a variety of forms, examples of which include fiber and granular.

In situations where the filter material is intended to solubilize and thereafter become part of the product that injected in the patient, the device may be configured to separate bone fragments using a separate device than the device in which the filter material is placed to minimize the potential of the bone fragments becoming associated with the injectable product.

The filter container 48 may have a filter membrane that is fabricated with a pore size that retains a desired portion of the bone fragments and the tissue within the filter container 48. For example, forming the filter membrane with a pore size of between about 20 microns and about 100 microns would facilitate retaining the bone fragments and a substantial portion of the progenitor cells in the filter container 48. The filter membrane may also be selected to remove portions from the aspirate that could potentially cause damage if placed in or near a joint.

In yet another configuration, the filter container 48 is selected to retain the bone fragments therein but substantially all of the remainder of the tissue flows into the collection vessel 30. The tissue in the collection vessel 30 may thereby include in addition to progenitor cells, red blood cells and other components that are not needed or potentially detrimental to forming the product. In such a situation, the red blood cells may be caused to separate from the remainder of the tissue such as mixing a material that causes the red blood cells to agglomerate and settle to the bottom of the collection vessel 30. More details on such a process are described later in this application.

Because of the challenges in aspirating the tissue that is collected in the collection vessel 30, it is desirable for substantially all of the aspirated tissue to be retained in the collection vessel 30 for further processing. To reduce the potential of loss of the aspirated tissue that is collected in the connective tissue progenitor cell harvesting and processing system 10, a hydrophilic membrane valve (not shown) may be attached to the first port 52 intermediate the tissue processing device 14 and the vacuum source.

The hydrophilic membrane valve allows the vacuum to pull gas therethrough until the hydrophilic membrane becomes wet such as when the connective tissue progenitor cell harvesting and processing system 10 is knocked over or the connective tissue progenitor cell harvesting and processing system 10 is overfilled with liquid. The hydrophilic membrane valve thereby prevents the aspirated tissue from being drawn out of the connective tissue progenitor cell harvesting and processing system 10.

To minimize the potential of the tissue processing device 14 being moved from a vertical orientation, the tissue processing device 14 may be placed in a base (not shown) having a width that is greater than the width of the tissue processing device 14. An example of one suitable technique that may be used to retain the tissue processing device 14 in a vertical orientation is described herein.

An alternative or additional technique to minimize the potential of aspirated tissue being drawn into the vacuum line may include attaching the tissue processing device 14 to an object proximate to the patient from which the tissue is being aspirated. An example of one suitable option is a clip that attaches the tissue processing device 14 to an IV pole, a drape near the patient or the operating table.

Prior to use, the components of the connective tissue progenitor cell harvesting and processing system 10 may be sterilized. A person of skill in the art will appreciate that a variety of sterilization techniques may be used. An example of one suitable sterilization technique is exposure of the packaged components to gamma radiation.

As an initial step in harvesting the tissue, the collection vessel cap 32 is attached to the collection vessel 30 so that the connective tissue progenitor cell harvesting and processing system 10 looks substantially as illustrated in FIG. 1. The tissue harvesting device 12 is attached to the tissue processing device 14 using the tubing 16. A vacuum source (not shown) is attached to the second port 52.

A site is selected from which the tissue is to be harvested. It is possible to use the invention in conjunction with harvesting tissue from a variety of bones in a patient. Preferred sites for harvesting the tissue include the iliac crest and pedicle/vertebral bodies.

Figure 3:
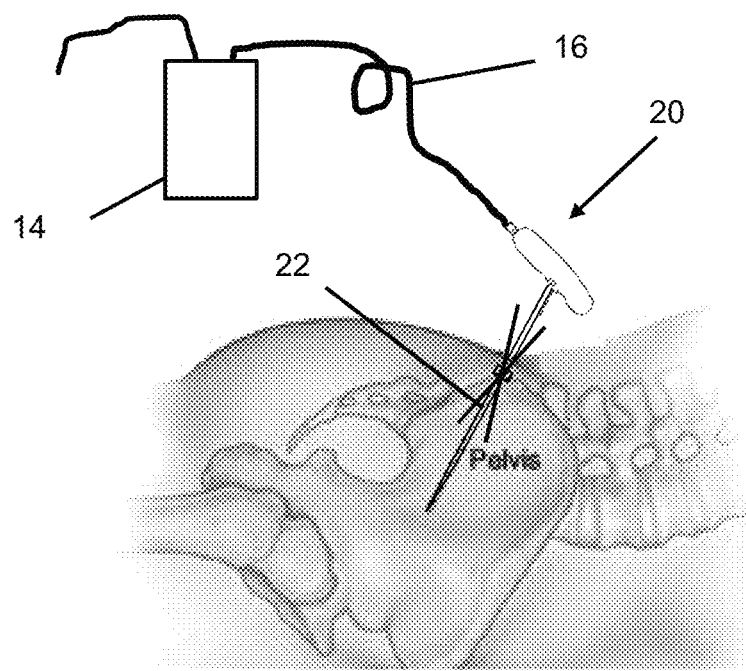
FIG. 3 is a schematic view of connective tissue progenitor cell harvesting system according to an embodiment of the invention where the needle is inserted into a patient's ilium.

The needle portion 22 is inserted into the bone as illustrated in FIG. 3. As the tip portion 24 contacts the outer surface of the bone, the tip portion 24 causes a hole to be formed through the hard outer surface of the bone. Once access to the interior of the bone is attained, the needle portion 22 is axially rotated to cause the tissue within the bone to be disrupted and such a process dissociates connective tissue progenitor cells within the bone. In certain embodiments, the needle portion 22 is inserted while the needle portion 22 is rotated and while a vacuum is applied to the tissue harvesting device 12. Alternatively, the needle portion 22 may be inserted a desired distance into the bone, rotated and then a vacuum applied in sequence.

During the process of extracting the tissue, the needle portion 22 may be partially withdrawn, pivoted and inserted in a different direction as illustrated in FIG. 3. Such a process increases the amount of tissue that is harvested from the patient. Using such a process it is desirable for the needle to flex but at the same time not break or remain in a deformed/deflected configuration.

To enhance the volume of tissue that can be aspirated, the needle portion 22 may be rotated as the distal end of the needle portion 22 moves through the interior of the bone. The movement disrupts the tissue inside the bone, which enhances the ability to withdraw the tissue. This process significantly increases the volume of beneficial tissue that can be harvested as compared to conventional processing techniques that merely insert the aspiration needle into the bone at different depths.

A vacuum is applied to the system, which causes the tissue to be aspirated through the needle portion 22. The aspirated tissue flow through the tubing 16 and into the tissue processing device 14. This process is continued until a desired volume of tissue has been aspirated from the patient.

If it is not possible to obtain a desired volume of the tissue from a particular location, it may be necessary to insert the needle portion 22 into a different location in the bone. It may also be necessary to insert the needle portion 22 into a different bone.

After aspiration, the tissue passes through the filter container 48, which retains substantially all of the aspirated bone fragments. As described above, the filter container 48 may include a filter membrane that selectively retains the connective tissue progenitor cells contained in the aspirate. The filter membrane may solubilize when it becomes wet to facilitate injection of the product thereby obtained while avoiding the need to separate the connective tissue progenitor cells from the filter material using further processing.

Alternatively or additionally, a centrifuge may be used to concentrate beneficial cells in the supernatant. A drawback of the centrifuge is the capital equipment cost. Also, the relatively harsh conditions of the centrifuge could result in increased cell damage. Another drawback of using centrifuge is challenges with ensuring sterility of the processed product.

Yet another technique that may be used for concentrating cells in the supernatant is a non-solubilizable membrane filter to achieve complete cell retention. The filter membrane would be selected to provide an appropriate porosity and/or selective properties. A drawback of the membrane filter is that it would require back-flushing to remove the connective tissue progenitor cells from the filter membrane. There can be challenges associated with obtaining a high concentration of cell recovery using the back-flushing. Additionally, the nature of the back-flushing process dilutes the concentration of the beneficial cells and could potentially lead to cell damage.

A difference between selective cell retention that is discussed above and complete cell retention that is discussed in other portions of this application is that selective cell retention is typically caused by cells adhering to the material whereas complete cell retention typically results from physical trapping of the cells.

It may be desirable to control the intensity of the vacuum that is pulled through the harvesting device 12. An example of one mechanism to control the vacuum level is using a valve that is operably attached to the vacuum line that is attached to the second port 52.

Figures 4, 5:
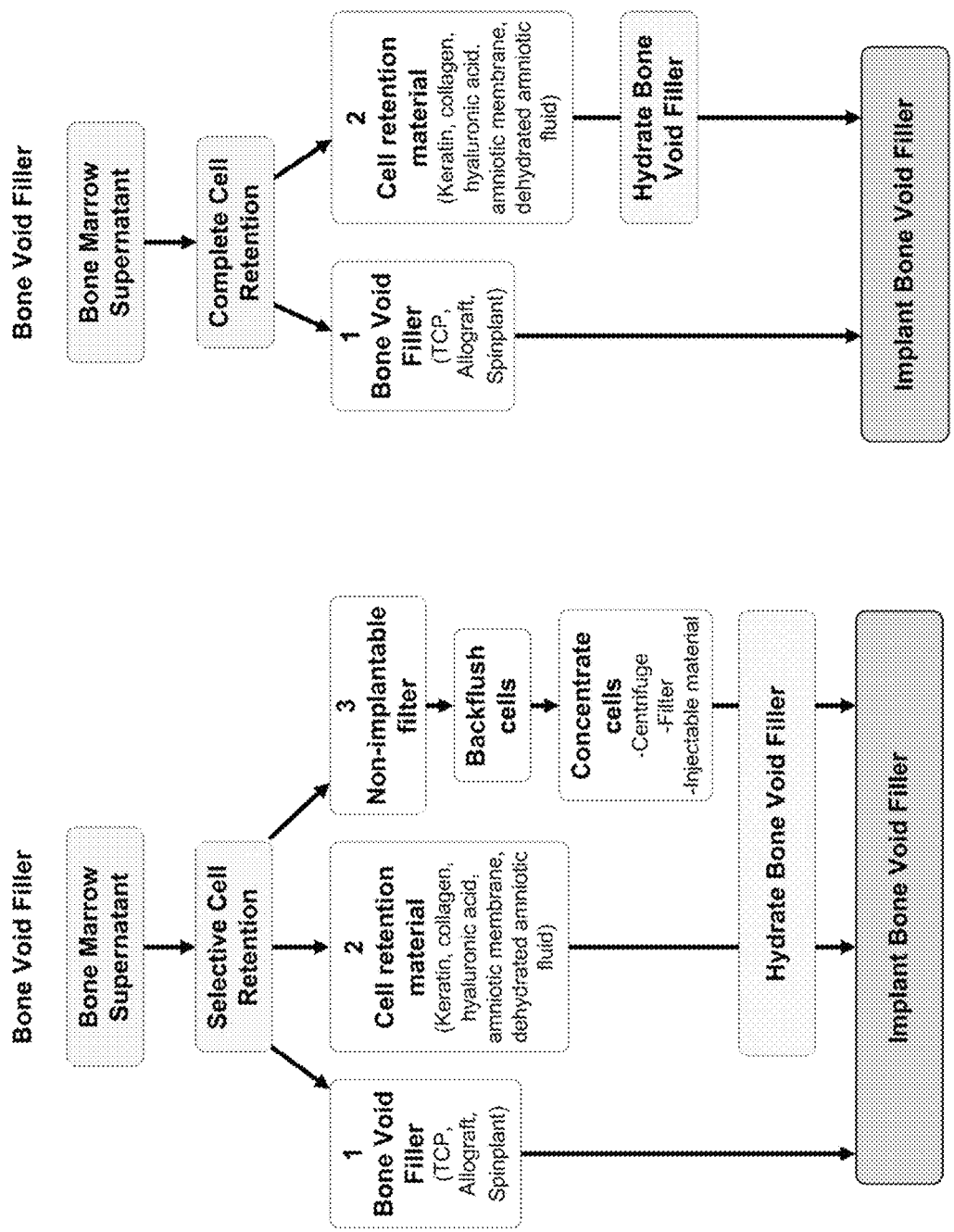
FIG. 4 is a flow chart illustrating the processes for forming the bone marrow into bone void filler that utilizes selective cell retention.
FIG. 5 is a flow chart illustrating the processes for forming the bone marrow into bone void filler that utilizes complete cell retention.

The various configuration of the method of the invention are depicted in FIGS. 4-7. The flow chart set forth in FIGS. 4 and 5 illustrates the use of a method according to an embodiment of the invention that is used to produce bone void filler. The bone marrow is either processed using selective cell retention (FIG. 4) or complete cell retention (FIG. 5).

As an initial step in both of these processes, the bone marrow may be processed to remove at least a portion of the red blood cells contained therein and thereby produce a supernatant. In certain embodiments, substantially all of the red blood cells are removed from the bone marrow. As used herein, substantially removing the red blood cells means that greater than about 90 percent of the red blood cells in the bone marrow are removed. As a result of this processing, the bone marrow is substantially devoid of red blood cells. An example of one suitable technique for removing at least a portion of the red blood cells is by mixing a binding agent with the bone marrow aspirate.

The binding agent should also be relatively inert with respect to the other desirable components in the bone marrow aspirate such that the binding agent does not impact the beneficial properties of the bone marrow aspirate.

Furthermore, the binding agent should have no negative interactions if any of the binding agent remains in the bone marrow aspirate, which then becomes incorporated into the bone graft and thereafter is implanted into the patient or the therapeutic composition that is injected into the patient.

An example of one such binding agent that may be used in conjunction with separating the red blood cells from the bone marrow aspirate is marketed under the designation PrepaCyte by BioE LLC from St. Paul, Minn. USA.

An advantage of using the red blood cell binding agent as compared to a conventionally used centrifuge is that the red blood cell binding agent removes more than about 90 percent by weight of the red blood cells in the aspirate and, in certain situations, more than about 99 percent by weight of the red blood cells in the aspirate.

In contrast, using the centrifuge to separate the red blood cells typically removes only about 60 percent by weight of the red blood cells in the aspirate unless higher centrifugal forces are utilized and such higher centrifugal forces increase the likelihood of damage to the connective tissue progenitor cells in the aspirate.

Another benefit of using the red blood cell binding agent is that a higher percentage of nucleated cells are retained in the aspirate (about 76 percent by weight) as compared to removing the red blood cells using a centrifuge (about 63 percent by weight).

The process set forth in column 1 in FIG. 4 utilizes a selective retention process. In this process, the bone marrow supernatant is passed through a material that is conventionally used in fabricating bone void fillers. Examples of such materials include tricalcium phosphate, allograft, Spinplant BioYarn, hydroxyapatite, calcium sulphate, or materials like OrthoRebirth Rebossis, which is a fiber form of tricalcium phosphate blended with poly-lactic acid or poly-gycolic acid or tricalcium phosphate blended with keratin or amniotic material etc.

The filter material may have an affinity for connective tissue progenitor cells. As the red blood cell depleted supernatant passes through the filter material, a significant portion of the connective tissue progenitor cells are selectively retained therein to thereby produce a cell rich bone graft material. In certain embodiments, substantially all of the connective tissue progenitor cells are retained in the filter material. As used herein, retaining substantially all of the connective tissue progenitor cells means that greater than about 90 percent of the connective tissue progenitor cells in the bone marrow are retained in the filter material.

The filter material may become a gel or hydrolyze into a fluid. This process may occur relatively quickly such as in less than about 10 minutes and, preferably in less than about 5 minutes. The gel and the fluid may be relatively viscous to facilitate retaining the bone void filler proximate the implant location.

The process set forth in column 2 in FIG. 4 utilizes a process that is similar to the process set forth in column 1 except that the filter material is a biomaterial that is currently not used as a bone void filler. Examples of these materials include keratin, collagen and hyaluronic acid. After the selective retention process, the resulting product may be hydrated such as through the addition of water to provide the bone void filler with a desired viscosity. In certain embodiments, a traditional bone void material such as tricalcium phosphate, allograft or Spinplant BioYarn may be mixed with this material before the bone void filler is implanted. The hydration that is associated with preparing the bone void filler is separate and distinct from hydrolysis that occurs when preparing the therapeutic composition used in conjunction with treating the soft tissue conditions.

The process set forth in column 3 in FIG. 4 utilizes a non-implantable selective retention filter to separate the connective tissue progenitor cells in the bone marrow supernatant. An example of one suitable non-implantable selective retention filter is commercially available from Kaneka. After the bone marrow supernatant is passed through the filter, the filter is back flushed such as using saline to separate the connective tissue progenitor cells from the filter. This process also causes the connective tissue progenitor cells to be resuspended.

Prior to use in forming the bone void filler, it may be desirable to concentrate the resuspended connective tissue progenitor cells. Examples of techniques that may be used to concentrate the resuspended connective tissue progenitor cells include centrifuge, filter or an injectable material. It may be desirable to hydrate this product and/or mix this product with a traditional bone void material such as tricalcium phosphate, allograft and Spinplant BioYarn before the bone void filler is ready to be implanted.

The process set forth in column 1 in FIG. 5 is similar to the process set forth in column 1 in FIG. 4 except that a filter material is used that retains substantially all of the cells in the bone marrow supernatant. Examples of filter material that may be used in this embodiment include stratified, sand and gravel-type filters.

The process set forth in column 2 in FIG. 5 is similar to the process set forth in column 2 in FIG. 4 except that a filter material is used that retains substantially all of the cells in the bone marrow supernatant. Similar to the process referenced in the preceding paragraph, the filter material used in this process may utilize stratified, sand and gravel-type filters. The biomaterial would be the filter and provide benefit to the cell/filter composite by helping to retain the beneficial cells.

Now moving to the process of preparing an injectable material that is suitable for intra- or extra-articular injection for use in treating soft tissue conditions, which is set forth in FIGS. 6 and 7. The bone marrow is either processed using selective cell retention (FIG. 6) or complete cell retention (FIG. 7).

A primary difference between a composition that is intended for intra-articular injection and a composition that is intended for extra-articular injection is that the material mixed with the connective tissue progenitor cells for intra-articular injection must be substantially non-abrasive to minimize the potential of joint damage caused by the abrasive nature of such material. In contrast, the material mixed with the connective tissue progenitor cells for extra-articular injection may have abrasive characteristics.

In view of this difference, it is generally possible to use a composition primarily intended for intra-articular injection in conjunction with an extra-articular injection. On the other hand, it may not be suitable to use a composition primarily intended for extra-articular injection in conjunction with an intra-articular injection.

The process set forth in column 1 in FIG. 6 utilizes a biomaterial to selectively filter the bone marrow supernatant. Examples of these materials include keratin, collagen and hyaluronic acid. After the selective retention process, the resulting product may be hydrated such as through the addition of water to provide the injectable material with a desired viscosity such as if the material is intended for injection.

The process set forth in column 2 in FIG. 6 utilizes a non-implantable selective retention filter to separate the connective tissue progenitor cells in the bone marrow supernatant. An example of one suitable non-implantable selective retention filter is commercially available from Kaneka. After the bone marrow supernatant is passed through the filter, the filter is back flushed such as using saline to separate the connective tissue progenitor cells from the filter. This process also causes the connective tissue progenitor cells to be resuspended.

Prior to injection, it may be desirable to concentrate the resuspended connective tissue progenitor cells. Examples of techniques that may be used to concentrate the resuspended connective tissue progenitor cells include centrifuge, filter or an injectable material.

The process set forth in column 1 in FIG. 7 is similar to the process set forth in column 1 except that a filter material is used that retains substantially all of the cells in the bone marrow supernatant. The filter material may be made an appropriate biomaterial such as collagen (that may be provided in a variety of forms, examples of which include fibers, sponge and particles), keratin (that may be provided in a variety of forms, examples of which include fibers and sponges), hyaluronic acid (that may be provided in a variety of forms, examples of which include fibers and sponges, amniotic membrane material, dehydrated amniotic membrane material and Spinplant BioYarn. The effective porosity of this filter would capture all non-plasma constituents. This configuration may provide lubrication to the joint, possibly express beneficial factors (platelet-derived growth factor, vascular endothelial growth factor, bone morphogenic proteins, etc.) and simplify the preparation process.

The processing set forth in column 2 in FIG. 7 utilizes filter with a porosity that is selected to capture a large portion of the non-serum blood components such as connective tissue progenitor cells, white blood cells and platelets. Thereafter, the filter is back flushed to remove the materials to separate these components from the filter. The resultant product may be concentrated such as using a centrifuge, filter or injectable material.

The process set forth in column 3 in FIG. 7 utilizes a centrifuge to concentrate the connective tissue progenitor cells, which is similar to the process utilized in conjunction with cord blood. A disadvantage of this process is that the centrifuge can damage the connective tissue progenitor cells.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention.

The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A method of treating soft tissue conditions comprising:
providing a harvesting device;
operably connecting the harvesting device to a tissue processing device using tubing;
forming an aperture in a bone, wherein the bone comprises an interior;
inserting the harvesting device through the aperture in the bone and into the interior of the bone;
manipulating the harvesting device to dissociate connective tissue progenitor cells in the interior of the bone;
aspirating tissue from the interior of the bone that contains the dissociated connective tissue progenitor cells and bone fragments;
removing substantially all of the bone fragments from the aspirated tissues to produce a bone fragment depleted aspirated tissue;
separating red blood cells from the bone fragment depleted aspirated tissue;
separating the connective tissue progenitor cells from the red blood cell depleted aspirated tissue using a solubilizable filter material;
solubilizing the filter material to form a solubilized product containing the separated connective tissue progenitor cells and the solubilized filter material, wherein the solubilized product is a fluid; and
injecting the solubilized product in an intra-articular region of a body that is experiencing a soft tissue condition to treat the soft tissue condition.

2. The method of claim 1, wherein manipulating the harvesting device morcelizes bone in the interior into bone fragments to dissociate the connective tissue progenitor cells from the bone and wherein the method further comprises separating the bone fragments from the aspirated tissue.

3. The method of claim 1, wherein the separating red blood cells from the aspirated tissue is done using a binding agent that is capable of selectively binding with the red blood cells in the aspirated tissue.

4. The method of claim 1, wherein the connective tissue progenitor cells are separated from the aspirated tissue using a filter material that is associated with the tissue processing device.

5. The method of claim 4, wherein the connective tissue progenitor cells are separated from the aspirated tissue using selective cell retention.

6. The method of claim 5, wherein at least a portion of the filter material comprises hydrogel to which the connective tissue progenitor cells selectively bind.

7. The method of claim 4, wherein the connective tissue progenitor cells are separated from the aspirated tissue using complete cell retention.

8. The method of claim 7, wherein the complete cell retention physically traps cells in the aspirated tissue.

9. The method of claim 5, wherein the filter material comprises a naturally occurring biocompatible material and wherein the naturally occurring biocompatible material comprises at least one of keratin, collagen, hyaluronic acid, chondroitin, glucosamine, amniotic fluid and tissue from an amniotic sac.

10. The method of claim 1, wherein the separated connective tissue progenitor cells are autologous.

11. A method of treating soft tissue conditions comprising:
providing a harvesting device;
operably connecting the harvesting device to a tissue processing device using tubing;
forming an aperture in a bone, wherein the bone comprises an interior;
inserting the harvesting device through the aperture in the bone and into the interior of the bone;
manipulating the harvesting device to dissociate connective tissue progenitor cells in the interior of the bone;
aspirating tissue from the interior of the bone that contains the dissociated connective tissue progenitor cells and bone fragments;
removing substantially all of the bone fragments from the aspirated tissues to produce a bone fragment depleted aspirated tissue;
separating red blood cells from the bone fragment depleted aspirated tissue using a binding agent that is capable of selectively binding with the red blood cells in the aspirated tissue;
separating the connective tissue progenitor cells from the aspirated tissue using a solubilizable filter material that is associated with the tissue processing device;
solubilizing the filter material to form a solubilized product containing the separated connective tissue progenitor cells and the solubilized filter material, wherein the solubilized product is a fluid; and
injecting the solubilized product in an intra-articular region of a body that is experiencing a soft tissue condition to treat the soft tissue condition.

12. The method of claim 11, wherein the connective tissue progenitor cells are separated from the aspirated tissue using selective cell retention.

13. The method of claim 12, wherein at least a portion of the filter material comprises hydrogel to which the connective tissue progenitor cells selectively bind.

14. The method of claim 11, wherein the connective tissue progenitor cells are separated from the aspirated tissue using complete cell retention that physically traps cells in the aspirated tissue.

15. The method of claim 11, wherein the filter material comprises a naturally occurring biocompatible material and wherein the naturally occurring biocompatible material comprises at least one of keratin, collagen, hyaluronic acid, chondroitin, glucosamine, amniotic fluid and tissue from an amniotic sac.

16. The method of claim 11, wherein the separated connective tissue progenitor cells are autologous.

17. The method of claim 1, wherein the soft tissue condition that is treated using the claimed method is osteoarthritis and inflamed/damaged ligaments.

18. The method of claim 11, wherein the soft tissue condition that is treated using the claimed method is osteoarthritis and inflamed/damaged ligaments.

* * * * *